(12) United States Patent
Smith et al.

(10) Patent No.: US 7,297,813 B2
(45) Date of Patent: Nov. 20, 2007

(54) REMOVAL OF ALKYL ALKANESULFONATE ESTERS FROM ALKANESULFONIC ACIDS AND OTHER ORGANIC MEDIA

(75) Inventors: Gary Smith, Collegeville, PA (US); Robert Cordova, Herrin, IL (US); Johnson C. H. Chen, King of Prussia, PA (US); Mabel Chen, West Chester, PA (US)

(73) Assignee: Arkema Inc., Philadelphia, PA (US)

( * ) Notice: Subject to any disclaimer, the term of this patent is extended or adjusted under 35 U.S.C. 154(b) by 722 days.

(21) Appl. No.: 10/912,274

(22) Filed: Aug. 5, 2004

(65) Prior Publication Data

US 2006/0030725 A1    Feb. 9, 2006

(51) Int. Cl.
  C07C 309/02    (2006.01)
  C07C 309/04    (2006.01)
  C07C 309/20    (2006.01)
  C07C 309/24    (2006.01)
  C07C 309/63    (2006.01)

(52) U.S. Cl. ........................................ 562/124; 558/44
(58) Field of Classification Search ................ 562/124; 558/44
See application file for complete search history.

(56) References Cited

U.S. PATENT DOCUMENTS

| 2,805,246 A | 9/1957 | Bourguignon et al. |
| 3,729,507 A | 4/1973 | Beazley et al. |
| 6,121,486 A | 9/2000 | Hommeltoft |
| 6,187,169 B1 | 2/2001 | Gernon et al. |
| 2002/0026075 A1 | 2/2002 | Gancet |

FOREIGN PATENT DOCUMENTS

| JP | 02085295 | 3/1990 |
| JP | 03127753 | 5/1991 |
| WO | 01/94303 | 6/2001 |

*Primary Examiner*—Rebecca Anderson
*Assistant Examiner*—Jason M Nolan
(74) *Attorney, Agent, or Firm*—Steven D. Boyd

(57) ABSTRACT

Methods of removing alkyl alkanesulfonate esters from aqueous or anhydrous compositions are provided. The invention provides methods for the conversion of alkyl alkanesulfonate esters of the formula $RSO_3R'$ to the corresponding acids of the formula $RSO_3H$. The alkyl alkanesulfonate esters are present in an organic medium, which may contain significant amounts of water or which may be anhydrous or substantially anhydrous. In some embodiments, the invention provides methods for purifying aqueous or anhydrous alkanesulfonic acids by removing alkyl alkanesulfonate esters.

31 Claims, No Drawings

REMOVAL OF ALKYL ALKANESULFONATE ESTERS FROM ALKANESULFONIC ACIDS AND OTHER ORGANIC MEDIA

FIELD OF THE INVENTION

The invention relates to alkanesulfonic acids. More particularly, it relates to methods of removing alkyl esters of these acids from compositions containing them, thereby purifying the compositions.

BACKGROUND OF THE INVENTION

Alkanesulfonic acids, particularly methanesulfonic acid (MSA), are typically prepared by reaction of a thiol or disulfide with a strong aqueous oxidant. A common oxidant for this chemistry is aqueous chlorine, with alternative oxidants including nitric acid and hydrogen peroxide/hydrogen halide. The alkanesulfonic acid products from these oxidation reactions are typically in an aqueous form. The purified commercial products are then sold as aqueous acids or anhydrous acids, the latter being typically obtained by distillation of the water from the sulfonic acid.

Processes for the distillation of water from aqueous methanesulfonic acid to produce anhydrous sulfonic acids, particularly anhydrous methanesulfonic acid, require high temperatures (120-190° C.) and reduced pressures (5-66 mbar) to effect the removal of the water and to obtain an anhydrous product. At these elevated temperatures, anhydrous or near-anhydrous alkanesulfonic acids are known to decompose to form alkyl alkanesulfonate esters, presumably via formation of the sulfonyl anhydride and subsequent decomposition to the alkyl alkanesulfonate ester and $SO_2$. In the case of methanesulfonic acid, the adventitiously formed methyl methanesulfonate is known to possess toxic or mutagenic properties, and its presence is therefore undesirable. Other alkyl esters of methanesulfonic acid have also been shown to exhibit high toxicity and mutagenic properties.

Alkanesulfonic acids are commonly used as catalysts for the esterification of weaker acids with alkanols, and in the preparation of ethers from alkanols. These reactions are normally driven to completion by removal of the water of condensation using distillation or liquid/liquid phase separation. In these reactions, esterification of the sulfonic acid catalyst can occur and thereby consume some of the sulfonic acid, which could otherwise be recycled for further use as a catalyst. Thus in such systems, as well as in the manufacture of alkanesulfonic acids, it would be desirable to provide ways of converting such sulfonate esters back to the acids, or to permit their facile removal.

SUMMARY OF THE INVENTION

The invention provides a method of removing alkyl alkanesulfonates $RSO_2OR'$ from a composition. The method includes contacting the composition with a reagent selected to convert the R' moiety or the OR' moiety of the $RSO_2OR'$ to one or more products selected from the group consisting of R'X, R'$SO_3$H, R'$SO_3M_n$, R'$SO_3^3$ R"R'"R""$NH^+$, R'$SO_3$R", R"-ZOR', $(HO)_2PO(OR')$, $HOPO(OR')_2$ $(R'O)_3$PO, $(M_nO)_2PO(OR')$, $M_nOPO(OR')_2$, $HO_3S$—R"-ZOR', $M_nO_3S$—R"-ZOR', $M_nO_3S$—R"(ZOM$_n$)-ZOR', oxidized carbon species, and water, thereby converting the $RSO_2OR'$ to $RSO_3H$. R and R' are each independently a $C_1$-$C_{20}$ alkyl, aralkyl or alkenyl group, or any of these incorporating a substituent selected from the group consisting of halogens and functional groups comprising oxygen, sulfur, silicon, tin, phosphorous, or nitrogen. R", R'" and R"" are independently a polymeric group or a $C_1$-$C_{20}$ alkyl, aryl, aralkyl or alkenyl group, or any of these incorporating a substituent selected form the group consisting of halogens and functional groups comprising oxygen, sulfur, silicon, tin, phosphorous, or nitrogen. M is a metal selected from the group consisting of Group I metals, Group II metals, transition metals, Al, Sn, Sb, Pb, and Bi, provided that M is a Group I or Group II metal when the product is $(M_nO)_2PO(OR')$, $M_nOPO(OR')_2$ or $M_nO_3S$—R"(ZOM$_n$)-ZOR', and n is equal to the reciprocal of the oxidation state of the metal. Z is CO, P(O)OH, P(O)OR' or S(O), and X is halogen.

DETAILED DESCRIPTION OF THE INVENTION

The invention provides methods for the conversion of alkyl alkanesulfonate esters of the formula $RSO_3R'$ to the corresponding acids of the formula $RSO_3H$. The sulfonate esters are present in an organic medium, which may contain significant amounts of water or which may be anhydrous or substantially anhydrous. As used herein, unless otherwise specified, "substantially anhydrous" means containing at most 5 wt % water, and "anhydrous" means containing at most 1 wt % water. In some embodiments, the organic medium may be the acid $RSO_3H$, or a mixture of the acid with water, in which $RSO_3R'$ is present as an impurity. In this case, the removal of the $RSO_3R'$ may be considered a purification of $RSO_3H$. Alkyl alkanesulfonate esters suitable for conversion to the corresponding acids include compounds $RSO_3R'$ wherein R and R' independently represent $C_1$-$C_{20}$ alkyl, arylalkyl, or alkenyl groups, optionally substituted with halogen (F, Cl, Br, I), oxygen, sulfur-, silicon, tin, phosphorous, or nitrogen. Typically the functional groups, if present, are halogen, ether, ester, sulfide, carboxamide, or sulfonamide groups.

The alkyl alkanesulfonate esters can be substantially or completely removed from the organic medium by any of several methods, including:

(a.) Treatment of aqueous alkanesulfonic acids containing alkanesulfonate esters with anhydrous or aqueous hydrogen halide.

(b.) Treatment of anhydrous or substantially anhydrous alkanesulfonic acids containing alkyl alkanesulfonates with anhydrous or substantially anhydrous hydrogen halides.

(c.) Treatment of aqueous alkanesulfonic acids containing alkyl alkanesulfonates with strong oxidants such as nitric acid, nitric oxide/dinitrogen tetroxide, hydrogen peroxide, organic peroxides, aqueous halogen, or ozone.

(d.) Treatment of anhydrous or substantially anhydrous alkanesulfonic acids containing alkyl alkanesulfonates with strong oxidants such as aqueous 70-90% nitric acid, anhydrous nitric oxide/dinitrogen tetroxide, organic peroxides, hydrogen peroxide, or ozone.

(e.) Treatment of aqueous alkanesulfonic acid containing alkyl alkanesulfonate esters with reactive forms of $SO_2$.

(f.) Treatment of aqueous alkanesulfonic acid containing alkyl alkanesulfonate esters with weaker acids, or salts thereof.

(g.) Treatment of aqueous alkanesulfonic acid containing alkyl alkanesulfonate esters with materials possessing both sulfonic acid and weaker-acid functionality, or salts thereof.

Compositions containing any amount of alkyl alkanesulfonate may be treated by the methods of this invention, resulting in very low levels of those materials after treatment. Typically the concentration of the alkyl alkanesulfonate prior to treatment will be between about 1% and 5 ppm by weight in the composition, more typically between about 500 and 5 ppm. After treatment, the compositions typically contain less than 1 ppm of these compounds. Each of the above-outlined methods will now be discussed in detail.

(a.) Treatment of compositions containing alkanesulfonate esters with anhydrous or aqueous hydrogen halide is one method of removing the esters. One useful example is removal of these materials from aqueous alkanesulfonic acids. Typical conditions for treating an alkanesulfonic acid containing an alkanesulfonate ester $RSO_3R'$ as an impurity include contacting the mixture with anhydrous or aqueous hydrogen halides at temperatures of 50° C. for a minimum of eight hours, or for two or more hours at a temperature of 70° C., under conditions where sufficient agitation is present to permit intimate contact of the hydrogen halide and the dissolved sulfonate ester. The reaction chemistry can be illustrated as follows:

$$RSO_3R'+HX \rightarrow RSO_3H+R'X$$

with X representing F, Cl, Br, or I, and R and R' as previously defined herein.

In that the rate of reaction of the sulfonate ester is temperature dependent, and given the preferred treatment times and temperatures cited above, alternate heating times, temperatures, and mixing conditions can be readily inferred by those skilled in the art in order to achieve sufficient conversion of the sulfonate ester to the acid.

One exemplary embodiment of the method is the removal of methyl or ethyl methanesulfonate impurities in methanesulfonic acid with hydrogen chloride or hydrochloric acid, affording methyl or ethyl chlorides as the reaction products. These alkyl chloride products are gases at most convenient reaction temperatures and thus are easily separated from the methanesulfonic acid, thereby affording a sulfonic acid that is substantially free of the ethyl or methyl methanesulfonate impurities.

The treatment is typically carried out at a temperature less than the boiling point of a water-HCl azeotrope, that temperature being about 108° C. at atmospheric pressure. Above the azeotrope temperature, HCl tends to be removed from the reaction mixture by boiling, and it is generally desirable to avoid this situation in order to avoid HCl losses. Higher temperatures may be suitable, however, if pressures greater than atmospheric are used, thereby increasing the boiling point.

The mode of addition of the hydrogen halide may include, but is not limited to, simple stirring of the alkanesulfonic acid containing the sulfonate ester impurities with aqueous hydrogen halide, bubbling anhydrous hydrogen halide gas through the alkanesulfonic acid, or saturating the alkanesulfonic acid with the hydrogen halide at pressures greater than 1 atmosphere. While the molar charge of hydrogen halide may be varied over a considerable range, the most economical amount is typically 1 to 10 molar equivalents relative to the amount of sulfonate ester impurity in the alkanesulfonic acid, preferably 1-3 times. Several methods of removing the volatile organic products of the reaction can be readily envisioned by those skilled in the art, thereby affording the sulfonic acid in a form that is substantially free of the sulfonate ester impurity. These include, but are not limited to, heating the reaction mixture under reduced pressure, or contacting the treated alkanesulfonic acid with air, nitrogen, or other gases to entrain the alkyl halide into the gas phase.

(b.) Anhydrous or substantially anhydrous compositions containing alkanesulfonate esters may be treated with anhydrous or substantially anhydrous hydrogen halides to remove the esters. One useful example is removal of these materials from anhydrous or substantially anhydrous alkanesulfonic acids. In general, the procedures, conditions, and explanations given under (a.) above are applicable to the treatment of anhydrous compositions. An especially useful embodiment involves the reaction of methyl or ethyl methanesulfonate impurities in anhydrous or substantially anhydrous methanesulfonic acid with hydrogen chloride, affording methyl or ethyl chlorides as gaseous reaction products that are readily separated from the methanesulfonic acid. These alkyl chloride products are gases at the reaction temperature and thus easily separated, thus affording a methanesulfonic acid that is substantially free of the methyl or ethyl methanesulfonate impurities.

The temperature for this treatment is typically greater than 50° C., more typically greater than 70° C. and usually less than 170° C. In that the amount of water present is minimal, the loss of the hydrogen halide via azeotropic distillation is minimized, thus allowing the use of higher temperatures than when significant amounts of water are present. However, at temperatures significantly exceeding this range, alkyl alkanesulfonate esters (e.g. methyl methanesulfonate) typically begin to form by thermal decomposition processes. It should be noted that the removal of alkyl alkanesulfonate esters from alkanesulfonic acids using HCl or other hydrogen halides offers certain advantages over attempts to remove them by hydrolysis of the ester. In the former reaction, the alkyl chloride/halide product is low boiling and reasonably inert to acid media as well as to strong oxidizing agents such as $O_2$, $H_2O_2$, $HNO_3$ or the various nitrogen oxides that might be present in the acid as impurities. In contrast, hydrolysis results in formation of alcohols and/or ethers (e.g. methanol and dimethyl ether), both of which are much more reactive to strong oxidizing agents and thus may be converted to more difficult-to-remove impurities.

(c.) Strong oxidants such as nitric acid, nitric oxide/dinitrogen tetroxide, hydrogen peroxide, organic peroxides, aqueous halogen, and ozone may also be used to remove alkyl alkanesulfonates from aqueous compositions. One useful example is removal of these materials from aqueous alkanesulfonic acids. Using methods similar to those of (a.) and (b.), the alkanesulfonic acid containing sulfonate ester impurities is treated with a strong oxidizing agent such that the sulfonate ester is converted to the corresponding sulfonic acid and oxidized carbon species such as CO, $CO_2$, alcohols, aldehydes, ketones, carboxylic acids, or other oxygen-containing species derived from the R' moiety. One especially useful treatment involves the reaction of alkyl alkanesulfonate impurities in aqueous alkanesulfonic acid, particularly methyl, ethyl, and propyl esters in aqueous methane-, ethane- or propanesulfonic acids, with nitric acid or nitric oxide/dinitrogen tetroxide mixtures, affording alkanesulfonic acid, oxidized carbon species, NO, and $N_2O$, along with smaller amounts of nitroalkane $R'NO_2$. Without wishing to be bound by any particular theory or explanation, it is believed that the reaction chemistries can be illustrated at least approximately as follows:

$$2HNO_3 \rightarrow H_2O_2+2NO_2$$

$$RSO_3R'+2HNO_3 \rightarrow RSO_3H+CO_2+2H_2O+2\ NO$$

$$RSO_3R'+3NO_2 \rightarrow RSO_3H+CO_2+H_2O+3NO$$

$$RSO_3R'+3H_2O_2 \rightarrow R'SO_3H+CO_2+4H_2O$$

The above equations are balanced in the exemplary case where R'=methyl, but it will be understood that analogous equations may be written for any R'. The temperature for such a treatment is typically greater than 0° C. and less than 220° C., preferably greater than 120° C. and less than 210° C. The mode of addition of the nitrogenous oxidant may include, but is not limited to, simple stirring of the alkanesulfonic acid containing the sulfonate ester impurities with aqueous concentrated nitric acid, or bubbling anhydrous nitric oxide/dinitrogen tetroxide gas through the alkanesulfonic acid. The molar charge of the oxidant is typically 2 to 10 molar equivalents relative to the amount of sulfonate ester impurity in the alkanesulfonic acid, preferably 2-6 times. Several methods to remove the volatile organic and inorganic products of the reaction can be readily envisioned by those skilled in the art, thereby affording the sulfonic acid in a form that is substantially free of the sulfonate ester impurity. These include, but are not limited to, heating under reduced pressure, or contacting to the treated alkanesulfonic acid with air, nitrogen, or other gases.

Other strong oxidants such as hydrogen peroxide, organic peroxides, ozone, or aqueous halogen may also be used in place of, or in addition to, nitrogenous oxidants such as described above, according to the invention.

(d.) Anhydrous or substantially anhydrous compositions containing alkyl alkanesulfonates may also be treated with strong oxidants such as aqueous 70-90% nitric acid, anhydrous nitric oxide/dinitrogen tetroxide, organic peroxides, hydrogen peroxide, and ozone to remove the alkanesulfonates. One useful example is removal of these materials from anhydrous or substantially anhydrous alkanesulfonic acids. In general, the procedures, conditions, and explanations given under (c.) above are applicable to the treatment of anhydrous compositions. One especially useful treatment involves the reaction of alkyl alkanesulfonate impurities in anhydrous or substantially anhydrous alkanesulfonic acid, particularly methyl, ethyl, and propyl esters in methane-, ethane- or propanesulfonic acids, with nitric acid or nitric oxide/dinitrogen tetroxide mixtures, affording alkanesulfonic acid, oxidized carbon species, NO, and $N_2O$, along with smaller amounts of nitroalkane $R'NO_2$. The reaction chemistries are as described under (c.) above. Since the amount of nitrogenous oxidant would be small relative to the amount of material being treated, 70-90% nitric acid is considered to be substantially anhydrous for the purposes of this invention. As noted above under (c.), the use of other strong oxidants such as hydrogen peroxide or ozone may also be suitable according to the present invention.

(e.) Treatment of aqueous mixtures containing alkyl alkanesulfonate esters may also be performed with reactive forms of $SO_2$, resulting in removal of the alkanesulfonate esters. One useful example is removal of these materials from aqueous alkanesulfonic acids. According to this embodiment of the invention, the R' portion (i.e. the alcohol-derived portion) of the alkyl alkanesulfonate is converted to an alkanesulfonic acid or salt. The reactive forms of $SO_2$ may include (i) gaseous $SO_2$, (ii) aqueous sulfurous acid, (iii) metal salts of sulfurous acid ($H_2SO_3$), (iv) amine salts of $H_2SO_3$, (v) alkyl sulfites, or (vi-ix) complexes of $SO_2$ with highly polar materials such as amines, carboxamides, sulfonamides, sulfones or sulfoxides. Complexes of $SO_2$ with polymers containing these polar functionalities can also be readily envisioned by those skilled in the art as having similar applicability, and may also be used. The net chemistries of exemplary embodiments are summarized below:

Reaction with gaseous $SO_2$ in aqueous media, e.g., aqueous sulfurous acid:

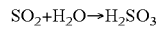

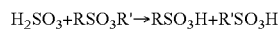

Reaction with a metal salt of sulfurous acid:

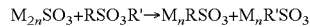

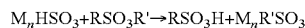

Reaction with an amine sulfite:

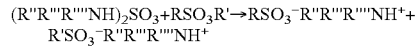

Reaction with an alkyl sulfite ester:

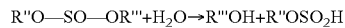

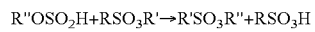

Reaction with an amine-$SO_2$ complex:

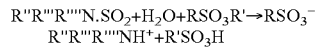

Reaction with a sulfonamide-$SO_2$ complex:

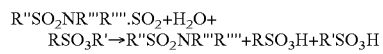

In the above equations, R and R' are as defined previously herein. R", R'" and R"" independently represent polymeric groups, hydrogen, $C_1$-$C_{20}$ alkyl, aralkyl or alkenyl group, or any of these incorporating a substituent selected from the group consisting of halogens and functional groups comprising oxygen, sulfur, silicon, tin, phosphorous, or nitrogen. If R" or R'" are alkyl, aryl, arylalkyl, or alkenyl, they are typically $C_1$-$C_{20}$ groups, optionally substituted as noted. M represents a Group I metal, a Group II metal, a transition metal, Al, Sn, Sb, Pb, or Bi, wherein n is the reciprocal of the oxidation state of the metal. Typically, a Group I and/or Group II metal will be used.

In that it is advantageous to easily separate the spent treating agent from the purified alkanesulfonic acid, in one embodiment the treating agent is in the form of an insoluble organic polymer, optionally on an inorganic supporting material, with incorporated functionality suitable for binding $SO_2$ or $H_2SO_3$, or salts of the latter. In this embodiment, the net functionalities of the polymer and/or inorganic support include either ionically-bound sulfite (for example as the ionic sulfites derived from aqueous sulfurous acid or metal hydrogen sulfites with amine-containing-polymers, e.g., polyethylenimines, polyetheramines, or poly(aminoalkyl acrylates), or covalently-bound or physically-absorbed species having sulfite ester, $SO_2$-amine, $SO_2$-sulfoxide, $SO_2$-sulfone or $SO_2$-sulfonamide functionalities. Suitable materials may also include $SO_2$ adducts derived from aromatic, aliphatic, or heterocyclic homo- or copolymers containing sulfonamide, sulfoxide, or sulfone functionality. Non-limiting examples of suitable sulfite esters include those derived from polymeric polyols, e.g. polyvinyl alcohol.

The temperature for these treatments is not critical, but is typically greater than −20° C., more typically greater than 50° C. and less than 170° C. Suitable times and temperatures may of course vary according to the particular reactants involved, and routine experimentation is sufficient to determine optimal conditions for any particular case. The molar charge of the reactive form of $SO_2$ is typically 2 to 10 molar equivalents relative to the amount of sulfonate ester impurity in the alkanesulfonic acid, more typically 2-6 times. Addition of the reactive form of $SO_2$ may be performed in several ways so as to permit intimate contact between the sulfonate ester impurity in the alkanesulfonic acid and the reactive form of $SO_2$. These include but are not limited to bubbling anhydrous sulfur dioxide gas through the aqueous alkanesulfonic acid, or stirring the aqueous alkanesulfonic acid with either sulfurous acid, a dialkyl sulfite, an amine-$SO_2$ complex, a sulfoxide-$SO_2$ complex, a sulfone-$SO_2$ complex, a sulfonamide-$SO_2$ complex, or a polymeric or inorganic species containing the previously described reactive forms of $SO_2$. Another alternative is to pass the aqueous alkanesulfonic acid through a fixed bed containing an $SO_2$-bearing polymeric material, optionally on an inorganic support.

(f.) Mixtures containing alkyl alkanesulfonate esters may be treated with weaker acids, or salts thereof, that are separable from the components of such mixtures. One useful example is removal of these materials from aqueous alkanesulfonic acids. Suitable weaker acids include phosphoric acid and acids containing carboxylic, phosphonic, or sulfinic acid functionality, or salts thereof, with treatment performed in such a way that the sulfonate ester impurities in the alkanesulfonic acid come into intimate contact with the weak-acid/salt species. The chemistries of four embodiments of this aspect of the invention, all involving a reaction between a sulfonate ester and a weak acids or its salt, can be summarized as follows:

$$RSO_3R'+R''\text{-}ZOH \rightarrow RSO_3H+R''\text{-}ZOR'$$

$$RSO_3R'+R''\text{-}ZOM_n \rightarrow RSO_3M_n+R''\text{-}ZOR'$$

$$RSO_3R'+(HO)_3PO \rightarrow RSO_3H+(HO)_2PO(OR')$$

$$RSO_3R'+(M_nO)_3PO \rightarrow RSO_3M_n+(M_nO)_2PO(OR')$$

In the above equations, Z represents —C(O)—, —P(O)OH—, —P(O)OR''— or —S(O)—; and R, R', R'', M, and n are as defined previously herein.

Suitable weak acid treating agents include phosphoric acid, oxalic acid, and any of (i.) aliphatic or aromatic carboxylic, phosphonic or sulfinic acids, (ii) these carboxylic, phosphonic or sulfinic species physically or chemically bound to an insoluble inorganic support, or (iii) polymeric resins containing carboxylic, phosphonic or sulfinic acid/salt functionalities, also optionally on an inorganic support. Examples of suitable weak acids include, but are not limited to, phosphoric acid, oxalic acid, $C_1$-$C_{20}$ aliphatic, aromatic, or heterocyclic carboxylic acids, benzenephosphonic acid, polymeric carboxylic acids such as polyacrylic acid, polymethacrylic acid, styrene-maleic acid copolymer, ethylene-maleic acid copolymer, and fluorinated or chlorinated analogs of these species.

In that it is advantageous to easily separate the spent treating agent from the purified alkanesulfonic acid, one especially useful embodiment employs a treating agent in a form that is physically or chemically bound to an insoluble inorganic support, or in the form of an insoluble organic polymer containing the appropriate functionality. In other embodiments, a carboxylic acid is chosen that is capable of forming a low-boiling ester that can be readily removed from the alkanesulfonic acid by distillation, evaporation or sublimation. In some embodiments, liquid/liquid extraction may be used to remove the resultant ester of the weak acid, and optionally remove residual amounts of the weak acid itself.

The temperature for the reaction between the alkyl alkanesulfonate and the weak acid (or metal salt thereof) is not critical, but is typically greater than −20° C., preferably greater than 20° C. and less than 170° C. Suitable times and temperatures may of course vary according to the particular reactants involved, and routine experimentation is sufficient to determine optimal conditions for any particular case. The molar charge of the reactive form of the treating agent is also not critical, but is typically from 1 to 100 molar equivalents relative to the amount of sulfonate ester impurity in the alkanesulfonic acid, preferably from 1-10 equivalents. Addition of the treating agent to the composition containing the alkanesulfonic acid may be performed in several ways so as to permit intimate contact between the sulfonate ester impurity in the alkanesulfonic acid and the treating agent. These include, but are not limited to, stirring the aqueous alkanesulfonic acid with the treating agent or passing the alkanesulfonic acid containing the sulfonate impurity through a fixed bed containing the treating agent. In the latter case, the use of a polymeric treating agent, or one with the treating agent on an insoluble inorganic support, is typically especially useful.

(g.) Treatment of aqueous compositions containing alkyl alkanesulfonate esters with materials possessing both sulfonic acid and weaker-acid functionality or salts thereof may be used, wherein the materials are separable from the alkanesulfonic acid. One example is removal of such esters from an aqueous alkanesulfonic acid. In general, the procedures and conditions given under (f.) above are applicable to the treatment of aqueous compositions with materials possessing both sulfonic acid and weaker-acid functionality.

The aqueous alkanesulfonic acid containing the alkyl alkanesulfonate ester impurity may be treated with a sulfonated species containing carboxylic, phosphonic, or sulfinic acid functionality, or a metal salt thereof, in such a way that the sulfonate esters impurities in the alkanesulfonic acid come into intimate contact with the sulfonated weak-acid/salt species.

The chemistries of three different embodiments of the invention involving reaction between a sulfonate ester and a sulfonated weaker acid or its salt can be summarized as follows:

$$RSO_3R'+HO_3S\text{—}R''\text{-}ZOH \rightarrow RSO_3H+HO_3S\text{—}R''\text{-}ZOR'$$

$$RSO_3R'+M_nO_3S\text{—}R''\text{-}ZOH \rightarrow RSO_3H+M_nO_3S\text{—}R''\text{-}ZOR'$$

$$RSO_3R'+M_nO_3S\text{—}R''(ZOM_n)\text{-}ZOH \rightarrow RSO_3H+M_nO_3S\text{—}R''(ZOM_n)\text{-}ZOR'$$

In the above equations, Z represents —C(O)—, —P(O)OH—, —P(O)OR'—, or —S(O)—; and R, R', R'', M, and n are as defined previously herein.

Sulfonated weak acids suitable for use as treating agents include aliphatic or aromatic carboxylic or phosphonic acids with sulfonic acid or sulfonyl substituents, and polymeric resins containing these functionalities, optionally on an inorganic support. Examples of these sulfonated weak acids include, but are not limited to, sulfoacetic acid, 2- or 3-sulfopropionic acid, sulfonated fatty acids, sulfosuccinic acid, 2,3-, or 4-sulfobenzoic acids, sulfophthalic acid, sulfonated benzenephosphonic acid, sulfonated styrene-maleic acid copolymer, and fluorinated or chlorinated analogs of these compounds.

In that it is advantageous to easily separate the spent treating agent from the purified product mixture, one especially useful embodiment is to use the treating agent in the form of an insoluble organic polymer containing the appropriate functionality, or in the form of a treating agent carried on an insoluble inorganic support.

One advantage of using certain of the embodiments listed above under (f.) and (g.) is that the alkyl alkanesulfonate is converted to the alkanesulfonic acid, thereby affording an improved yield of the acid. Other embodiments of (f.) and (g.), by virtue of forming a metal salt that incorporates the R' moiety, may provide convenient ways of removing that moiety from the reaction mixture, for example by precipitation and filtration to remove an insoluble metal salt.

In addition to removing alkyl alkanesulfonate esters from alkanesulfonic acids, for example as a means of purifying the acids, such esters may be instead be removed from other mixtures, according to the invention. In one such example, the sulfonate ester is formed as a side product or by-product during the use of an alkanesulfonic acid as a catalyst or solvent in an esterification, etherification, alkylation, or other reaction. Suitable modifications of the procedures outlined above, particularly methods (e.), (f.) and (g.), will be apparent to the skilled artisan, and are also contemplated according to the invention.

Treatments such as are described above under methods (a.) through (g.) may be of particular value in applications where the distillation of anhydrous or substantially anhydrous alkanesulfonic acids is performed, or in applications where water is removed from aqueous alkanesulfonic acids by high temperature distillation to afford anhydrous or substantially anhydrous alkanesulfonic acids. As discussed above, these operations can result in the undesired formation of alkyl alkanesulfonates.

The above methods (a.) through (g.) may be employed for removing sulfonate esters from alkanesulfonic acids manufactured by any means. Nonetheless, some methods may of course be more easily implemented in some manufacturing facilities than in others. As an example, since HCl is a by-product in the manufacture of alkanesulfonic acids from the oxidation of thiols or disulfides with chlorine and water, methods (a.) and (b.) are well suited for production facilities preparing the alkanesulfonic acids using $Cl_2$/HCl chemistries. Similarly, methods (c.) and (d.) may be of particular value for removing alkyl alkanesulfonates from anhydrous or aqueous alkanesulfonic acids manufactured using nitric acid as the oxidizing agent.

EXAMPLES

Example 1

Reaction of Methyl Methanesulfonate with HCl in Aqueous 70% Methanesulfonic Acid at 70° C. (According to Process (a.) Above)

A sample of 70% methanesulfonic acid was sparged with anhydrous HCl gas to afford a saturated solution. A weighed portion of this HCl saturated methanesulfonic acid (MSA) was transferred to a capped 33-mL vial. Methyl methanesulfonate (MMS) was added with mixing to afford a solution with a nominal initial MMS concentration of 138 ppm. Headspace gas chromatographic analysis revealed that methyl chloride was the principal organic component, with only small amounts (<2%) methanol and dimethyl ether.

Seven 2.5-gram aliquots were then taken from the initial mixture and immediately transferred to 10-mL Erlenmeyer flasks fitted with magnetic stirring bars and screw caps. After filling, each Erlenmeyer flask was immediately capped and placed in a preheated 70° C. oil bath mounted on a 9 position stirring hot plate. Individual flasks were then removed after 10, 17, 20, 40, 80, 120, and 180 minutes. Upon removal from the oil bath, each sample was immersed in an ice bath for 1 minute. Dichloromethane (5 mL) was then added and the flask re capped and shaken. The two phases were allowed to separate and the dichloromethane phase removed by pipette. The wet dichloromethane extract was dried with sodium sulfate, then analyzed by gas chromatography. Essentially complete reaction of the MMS had occurred after 120 minutes, as tabulated below.

| Time (min.) | Residual MMS (ppm) |
| --- | --- |
| 0 | 138 |
| 10 | 111 |
| 17 | 62 |
| 20 | 51 |
| 40 | 33 |
| 80 | 9 |
| 120 | <1 |
| 180 | <1 |

Example 2

Reaction of Methyl Methanesulfonate with HCl in Aqueous 25° C. (According to Process (a.) Above)

The procedure described in Example 1 was repeated with the exception that the reaction mixtures were held at 25° C. Essentially complete reaction of the MMS was found to require about 72 hours, as tabulated below.

| Time (hour) | Residual MMS (ppm) |
| --- | --- |
| 0 | 138 |
| 48 | 48 |
| 72 | <1 |

Comparative Example 3

Hydrolysis at Ambient Temperature of Methyl Methanesulfonate in 70% Methanesulfonic Acid A sample of 70% methanesulfonic acid initially containing 7 ppm methyl methanesulfonate was allowed to stand at ambient laboratory temperatures for 13 months. After extraction and analysis as in Example 1, the residual methyl methanesulfonate was found to be 0.6 ppm. Thus, hydrolysis of the sulfonate ester proceeds at a largely negligible rate under ambient conditions.

Example 4

Oxidation with Methyl Methanesulfonate with $HNO_3$ (According to Process (c.) Above)

A sample of 70% methanesulfonic acid initially containing 0.2% of methyl methanesulfonate impurity was treated with aqueous 70% HNO₃ at the temperatures and for the times tabulated below. The rate of reaction of the methyl ester was found to depend on temperature and nitric acid charge, as tabulated below.

| 70% HNO₃ Charge (ppm in 70% MSA) | Reaction Temperature (° C.) | Reaction Time (hr) | Initial MMS (ppm in 70% MSA) | Final MMS (ppm in 70% MSA) |
|---|---|---|---|---|
| 500 | 130 | 2 | 2000 | 1600 |
| 3600 | 130 | 2 | 2000 | 140 |
| 4700 | 200 | 2 | 2000 | <1 |

Example 5

Reaction of Sulfonate Esters in Esterification Products by with Metal Salts of Carboxylic Acids (According to Process (f.) Above)

An esterification reaction mixture (94 g), consisting of butanol (ca., 4.9% w/w), butyl stearate (95.1% w/w), residual stearic acid (trace), residual methanesulfonic acid catalyst (1383 ppm) and undesired butyl methanesulfonate (613 ppm) was treated with 45% aqueous KOH (229 mg, 1.84 mmol as compared to 1.74 mmol MSA originally charged to the reaction). The resulting mixture was heating at 50° C. for 40 minutes. Without wishing to be bound by any particular theory or explanation, it is believed that reaction of butyl stearate with KOH produced potassium stearate, which retains significant solubility in the butyl stearate medium. The formed potassium stearate then reacted with butyl methanesulfonate to produce potassium methanesulfonate and butyl stearate. After filtration of the by-product solid salts (0.6325 g), analysis of the mixture by gas chromatography revealed only 300 ppm unreacted butyl methanesulfonate, a 51% reduction.

Repetition of the above KOH treatment at a higher temperature (175° C./60 min.) revealed complete reaction of the butyl methanesulfonate. Similarly, treatment with NaOH was found equally effective as treatment with KOH. Treatment with Ca(OH)₂ proved ineffective, presumably due to formation of poorly soluble calcium salts. Treatment with acidic tin(II) or zirconium (IV) salts resulted in formation of additional butyl methanesulfonate.

Example 6

Reaction of Sulfonate Esters in Dialkyl Phthalate Esterification Products

Methyl methanesulfonate (MMS), methyl para-toluenesulfonate (MTS), butyl methanesulfonate (BMS), or butyl para-toluenesulfonate (BTS) was combined with either dimethyl phthalate (DMP) or dibutyl phthalate (DBP) to obtain initial mixtures with 55-148 ppm (w/w) sulfonate ester as tabulated below. The mixtures were then heated with vigorous stirring to 180° C., then cooled to 90° C. to simulate general esterification conditions. After such preparation, the resulting mixtures would have compositions similar to those observed in crude esterification product mixtures from typical commercial manufacturing processes. An aliquot of each mixture was taken at this point to represent the material prior to hydrolysis (i.e., time "0"). The hydrolysis medium was then added (30 ml water, aqueous 10% NaOH, or aqueous 10% Na₂CO₃) and the stirred mixture was maintained at 90° C. Aliquot samples were taken at the times specified in the table below. Each aliquot was extracted with diethyl ether, and the ether extracts washed with water, dried, and evaporated under vacuum to obtain the dry phthalate ester with residual sulfonate ester. The latter were then analyzed by gas chromatography to determine the amount of residual sulfonate ester.

| Phthalate Ester | Sulfonate Ester | Initial Sulfonate ester Before Heating (ppm w/w) | Hydrolysis Medium | Residual Sulfonate ester (ppm by weight) in Phthalate ester after Hydrolysis Time (min.) | | | | | |
|---|---|---|---|---|---|---|---|---|---|
| | | | | 0 | 15 | 30 | 60 | 120 | 180 |
| DMP 200 ml | MMS | 55 | Water | 34 | | 15 | 10 | 5.2 | 1.3 |
| DMP 200 ml | MTS | 95 | Water | 101 | | 98 | 93 | 93 | 83 |
| DBP 200 ml | BMS | 55 | Water | 51 | | 35 | 34 | 31 | 23 |
| DBP 200 ml | BTS | 84 | Water | 81 | | 78 | 76 | 76 | 72 |
| DMP 100 ml | MMS | 136 | Aq. NaOH | 68 | 4 | — | <1 | <1 | — |
| DMP 200 ml | MTS | 97 | Aq. NaOH | 70 | | 64 | 53 | 40 | 24 |
| DBP 200 ml | BMS | 48 | Aq. NaOH | 18 | 13 | — | 14 | 10 | — |
| DBP 200 ml | BTS | 84 | Aq. NaOH | 61 | | 59 | 59 | 54 | 55 |
| DMP 100 ml | MMS | 148 | Aq. Na₂CO₃ | — | 3 | — | <1 | <1 | — |
| DBP 100 ml | BMS | 96 | Aq. Na₂CO₃ | 30 | 33 | — | 31 | 17 | — |

As can be seen by reviewing the above data, reaction of the sulfonate esters derived from catalytic sulfonic acids used in typical esterifications is slower when using water as the treatment medium. The rate was accelerated on addition of alkaline base. Moreover, reaction rates for methyl and butyl methanesulfonates are faster than those for the corresponding toluenesulfonates, while those for the methyl methanesulfonates or toluenesulfonates were generally much faster than those for the corresponding butyl esters. As similarly proposed in Example 5 and without wishing to be bound by any particular theory or explanation, the acceleration is thought to arise from formation of the phthalate half ester/salt by reaction with the aqueous base with the dialkyl phthalate. The thus formed phthalate half ester/salt would retain significant solubility in the dialkyl phthalate phase, wherein it would react with the sulfonate ester. The slower reaction rates for the methanesulfonates vs. the toluenesulfonates, and for the methyl sulfonates vs. the butyl sulfonates, is consistent with the reduced molecular-scale steric interactions that arise when a smaller sulfonate ester (e.g., methyl sulfonates vs. butyl sulfonates, or methanesulfonate esters vs. toluenesulfonate esters) must react with the bulky phthalate half ester/salts. The alternative mechanism would be direct reaction of the sulfonate esters with hydroxide. The observed reaction rates are less consistent with the results one would expect for reaction of a small, unhindered nucleophile such as hydroxide with the various sulfonate esters.

Although the invention is illustrated and described herein with reference to specific embodiments, it is not intended that the subjoined claims be limited to the details shown. Rather, it is expected that various modifications may be made in these details by those skilled in the art, which modifications may still be within the spirit and scope of the claimed subject matter and it is intended that these claims be construed accordingly.

What is claimed:

1. A method of removing $RSO_2OR'$ from a composition, the method comprising contacting the composition with a reagent selected to convert the R' moiety or the OR' moiety of the $RSO_2OR'$ to one or more products selected from the group consisting of R'X, $R'SO_3H$, $R'SO_3M_n$, $R'SO_3^-R''R'''R''''NH^+$, $R'SO_3R''$, $R''\text{-}ZOR'$, $(HO)_2PO(OR')$, $HOPO(OR')_2$, $(R'O)_3PO$, $(M_nO)_2PO(OR')$, $HO_3S\text{—}R''\text{-}ZOR'$, $M_nO_3S\text{—}R''\text{-}ZOR'$, $M_nO_3S\text{—}R''(ZOM_n)\text{-}ZOR'$, oxidized carbon species, and water, thereby converting the $RSO_2OR'$ to $RSO_3H$;

wherein R and R' are each independently a $C_1$-$C_{20}$ alkyl, aralkyl or alkenyl group, or any of these incorporating a substituent selected from the group consisting of halogens and functional groups comprising oxygen, sulfur, silicon, tin, phosphorus, or nitrogen; R'' is a polymeric group or a $C_1$-$C_{20}$ alkyl, aryl, aralkyl or alkenyl group, or any of these incorporating a substituent selected from the group consisting of halogens and functional groups comprising oxygen, sulfur, silicon, tin, phosphorus, or nitrogen; R''' and R'''' are independently a polymeric group, hydrogen or a $C_1$-$C_{20}$ alkyl, aryl, aralkyl or alkenyl group, or any of these incorporating a substituent selected from the group consisting of halogens and functional groups comprising oxygen, sulfur, silicon, tin, phosphorus, or nitrogen; M is a metal selected from the group consisting of Group I metals, Group II metals, transition metals, Al, Sn, Sb, Pb, and Bi, provided that M is a Group I or Group II metal when the product is $(M_nO)_2PO(OR')$, $M_n$ OPO $(OR')_2$ or $M_nO_3S\text{—}R''(ZOM_n)\text{-}ZOR'$; n is equal to the reciprocal of the oxidation state of the metal; Z is CO, P(O)OH, P(O)OR'', or S(O); and X is halogen.

2. The method of claim 1, wherein the composition consists essentially of $RSO_2OR'$, $RSO_3H$ and water.

3. The method of claim 2, wherein the $RSO_2OR'$ is present before said converting at a starting level of between 1% and 5 ppm by weight, and is present after said converting at a level of less than 1 ppm by weight.

4. The method of claim 1, wherein the one or more products comprises $R'SO_3M_n$, wherein M is a Group I metal or a Group II metal, and wherein the step of contacting comprises contacting the composition with $HSO_3M_n$ to cause a reaction according to the equation:

$HSO_3M_n + RSO_3R' \rightarrow RSO_3H + R'SO_3M_n$.

5. The method of claim 1, wherein the one or more products comprises $R'SO_3M_n$, wherein M is a Group I metal or a Group II metal, and wherein the step of contacting comprises contacting the composition with $M_{2n}SO_3$ to cause a reaction according to the equations:

$M_{2n}SO_3 + RSO_3R' \rightarrow RSO_3M_n + R'SO_3M_n$.

6. The method of claim 1, wherein the one or more products comprises R'X, and wherein the step of contacting comprises contacting the composition with HX to cause a reaction according to the equation:

$RSO_3R' + HX \rightarrow RSO_3H + R'X$.

7. The method of claim 6, wherein the converting is performed under anhydrous conditions.

8. The method of claim 1, wherein the one or more products comprises an oxidized carbon species and water, and wherein the contacting comprises contacting the composition with $HNO_3$, nitric oxide, dinitrogen tetroxide, or a mixture of any of these.

9. The method of claim 8, wherein the contacting is performed under anhydrous conditions.

10. The method of claim 1, wherein the one or more products comprises an oxidized carbon species and water, and wherein the contacting comprises contacting the composition with hydrogen peroxide.

11. The method of claim 1, wherein the one or more products comprises an oxidized carbon species and water, and wherein the contacting comprises contacting the composition with an organic peroxide.

12. The method of claim 1, wherein the one or more products comprises an oxidized carbon species and water, and wherein the contacting comprises contacting the composition with aqueous halogen.

13. The method of claim 1, wherein the one or more products comprises an oxidized carbon species and water, and wherein the contacting comprises contacting the composition with ozone.

14. The method of claim 1, wherein the one or more products comprises $R'SO_3H$, and wherein the step of contacting comprises contacting the composition with $H_2SO_3$ to cause a reaction according to the equation:

$H_2SO_3 + RSO_3R' \rightarrow RSO_3H + R'SO_3H$.

15. The method of claim 1, wherein the one or more products comprises $R'SO_3^-R''R'''R''''NH^+$, and wherein the step of contacting comprises contacting the composition with $(R''R'''R''''NH)_2SO_3$ to cause a reaction according to the equation:

$(R''R'''R''''NH)_2SO_3 + RSO_3R' \rightarrow RSO_3^-R''R'''R''''NH^+ + R'SO_3^-R''R'''R''''NH^+$.

16. The method of claim 1, wherein the one or more products comprises $R'SO_3^-R''R'''R''''NH^+$, and wherein the step of contacting comprises contacting the composition with $R''R'''R''''N.SO_2$ and $H_2O$ to cause a reaction according to the equation:

$R''R'''R''''N.SO_2 + H_2O + RSO_3R' \rightarrow R'SO_3^- R''R'''R''''NH^+ + R'SO_3H$.

17. The method of claim 1, wherein the one or more products comprises $R'SO_3R''$, and wherein the step of contacting comprises contacting the composition with $H_2O$ and a component selected form the group $R''O\text{—}SO\text{—}OR'''$ or $R''OSO_2H$ to cause reactions according to the equations:

$R''O\text{—}SO\text{—}OR''' + H_2O \rightarrow R''OSO_2H + R'''OH$ $R''OSO_2H + RSO_3R' \rightarrow R'SO_3R'' + RSO_3H$.

18. The method of claim 1, wherein the one or more products comprises $R'SO_3H$, and wherein the step of contacting comprises contacting the composition with R"SO$_2$NR'"R"".SO$_2$ and H$_2$O to cause a reaction according to the equation:

$$R"SO_2NR'"R"".SO_2+H_2O+RSO_3R' \rightarrow R"SO_2NR'"R""+RSO_3H+R'SO_3H.$$

19. The method of claim 1, wherein the one or more products comprises R'SO$_3$H, and wherein the step of contacting comprises contacting the composition with water and the SO$_2$ complex derived from either a carboxamide of formula R"CO2NR'"R"", a sulfone of formula R"SO$_2$R'" or a sulfoxide of formula R"SOR'".

20. The method of claim 1, wherein the one or more products comprises R"-ZOR', and wherein the step of contacting comprises contacting the composition with R"-ZOH to cause a reaction according to the equation:

$$RSO_3R'+R"-ZOH \rightarrow RSO_3H+R"-ZOR'.$$

21. The method of claim 1, wherein the one or more products comprises R"-ZOR', and wherein the step of contacting comprises contacting the composition with R"-ZOM$_n$ to cause a reaction according to the equation:

$$RSO_3R'+R"-ZOM_n \rightarrow RSO_3M_n+R"-ZOR'.$$

22. The method of claim 1, wherein the one or more products comprises (HO)$_2$PO(OR'), and wherein the step of contacting comprises contacting the composition with (HO)$_3$PO to cause a reaction according to the equation:

$$RSO_3R'+(HO)_3PO \rightarrow RSO_3H+(HO)_2PO(OR').$$

23. The method of claim 1, wherein the one or more products comprises HOPO(OR')$_2$, and wherein the step of contacting comprises contacting the composition with (HO)$_2$PO(OR') to cause a reaction according to the equation:

$$RSO_3R'+(HO)_2PO(OR') \rightarrow RSO_3H+HOPO(OR')_2.$$

24. The method of claim 1, wherein one or more products comprises metal salts of phosphoric acid, or metal salts of the phosphoric acid esters of the formula HOPO(OR')$_2$.

25. The method of claim 1, wherein the one or more products comprises (R'O)$_3$PO, and wherein the step of contacting comprises contacting the composition with HOPO(OR')$_2$ to cause a reaction according to the equation:

$$RSO_3R'+HOPO(OR')_2 \rightarrow RSO_3H+(R'O)_3PO.$$

26. The method of claim 1, wherein one or more products comprises metal salts of phosphoric acid, metal salts of the phosphoric acid esters of the formula (R'O)$_3$PO.

27. The method of claim 1, wherein the one or more products comprises HO$_3$S—R"-ZOR', and wherein the step of contacting comprises contacting the composition with HO$_3$S—R"-ZOH to cause a reaction according to the equation:

$$RSO_3R'+HO_3S-R"-ZOH \rightarrow RSO_3H+HO_3S-R"-ZOR'.$$

28. The method of claim 1, wherein one or more products comprises metal salts of phosphoric acid, metal salts of the phosphoric acid esters of the formula HO$_3$S—R"-ZOR'.

29. The method of claim 1, wherein the one or more products comprises M$_n$O$_3$S—R"-ZOR', and wherein the step of contacting comprises contacting the composition with M$_n$O$_3$S—R"-ZOH to cause a reaction according to the equation:

$$RSO_3R'+M_nO_3S-R"-ZOH \rightarrow RSO_3H+M_nO_3S-R"-ZOR'.$$

30. The method of claim 1, wherein the one or more products comprises M$_n$O$_3$S—R"(ZOM$_n$)-ZOR', and wherein the step of contacting comprises contacting the composition with M$_n$O$_3$S—R"(ZOM$_n$)-ZOH to cause a reaction according to the equation:

$$RSO_3R'+M_nO_3S-R"(ZOM_n)-ZOH \rightarrow RSO_3H+M_nO_3S-R"(ZOM_n)-ZOR'.$$

31. The method of claim 1, wherein R is methyl and R' is methyl, ethyl, or a combination of these.

* * * * *